United States Patent
Hayakawa et al.

(10) Patent No.: US 11,060,061 B2
(45) Date of Patent: Jul. 13, 2021

(54) IMMORTALIZED SWEAT GLAND MYOEPITHELIAL CELL

(71) Applicants: MANDOM CORPORATION, Osaka (JP); OSAKA UNIVERSITY, Suita (JP)

(72) Inventors: Tomohisa Hayakawa, Suita (JP); Ryuichiro Kurata, Osaka (JP); Fumitaka Fujita, Osaka (JP); Fumihiro Okada, Osaka (JP); Kiyotoshi Sekiguchi, Suita (JP)

(73) Assignees: MANDOM CORPORATION, Osaka (JP); OSAKA UNIVERSITY, Suita (JP)

(*) Notice: Subject to any disclaimer, the term of this patent is extended or adjusted under 35 U.S.C. 154(b) by 0 days.

(21) Appl. No.: 16/626,052

(22) PCT Filed: Aug. 7, 2018

(86) PCT No.: PCT/JP2018/029594
§ 371 (c)(1),
(2) Date: Dec. 23, 2019

(87) PCT Pub. No.: WO2019/031500
PCT Pub. Date: Feb. 14, 2019

(65) Prior Publication Data
US 2020/0385680 A1 Dec. 10, 2020

(30) Foreign Application Priority Data
Aug. 9, 2017 (JP) .............................. JP2017-154503

(51) Int. Cl.
*C12N 5/077* (2010.01)
*C12N 15/85* (2006.01)
*C12N 15/86* (2006.01)

(52) U.S. Cl.
CPC .......... *C12N 5/0661* (2013.01); *C12N 15/85* (2013.01); *C12N 15/86* (2013.01); *C12N 2510/04* (2013.01); *C12N 2513/00* (2013.01)

(58) Field of Classification Search
CPC .......... A01K 67/0276; A01K 2217/075; A01K 2217/15; A01K 2227/105; C12N 5/0661; C12N 15/85; C12N 15/86; C12N 2510/04; C12N 2513/00
See application file for complete search history.

(56) References Cited

U.S. PATENT DOCUMENTS

2016/0075995 A1    3/2016   Kobielak

FOREIGN PATENT DOCUMENTS

FR    2 248 889 A1 *  5/2009   ............... C12N 5/10
JP    2014-503190 A    2/2014
WO    2012/059223 A1   5/2012

OTHER PUBLICATIONS

Kurata et al., "Isolation and Characterization of Sweat Gland Myoepithelial Cells from Human Skin", Cell Structure and Function, 2014, vol. 39, pp. 101-112, cited in Specification, ISR, JP Notice of Reasons for Refusal and Decision to Grant a Patent (12 pages).
Lee et al., "NCL-SG3: a human eccrine sweat gland cell line that retains the capacity for transepithelial ion transport", Journal of Cell Science, 1989, vol. 92, pp. 241-249, cited in Specification (12 pages).
Miyoshi et al., "In vitro expansion and genetic modification of gastrointestinal stem cells in spheroid culture", Nature Protocols, 2013, vol. 8, No. 12, pp. 2471-2482, cited in ISR (14 pages).
Koo et al., "Controlled gene expression in primary Lgr5 organoid cultures", Nature Methods, 2012, vol. 9, No. 1, pp. 81-83, cited in ISR (4 pages).
Kurata et al., "Three-dimensional cell shapes and arrangements in human sweat glands as revealed by whole-mount immunostaining", PLoS One, Jun. 21, 2017, vol. 12, No. 6, pp. 1-17, cited in ISR (17 pages).
Yao et al., "Identification of a new sweat gland progenitor population in mice and the role of their niche in tissue development", Biochemical and Biophysical Research Communications, 2016, vol. 479, No. 4, pp. 670-675, cited in ISR (6 pages).
Bhise et al., "The relationship between terminal functionalization and molecular weight of a gene delivery polymer and transfection efficacy in mammary epithelial 2-D cultures and 3-D organotypic cultures", Biomaterials, 2010, vol. 31, pp. 8088-8096, cited in ISR (9 pages).
Li et al., "Three-dimensional culture and identification of human eccrine sweat glands in matrigel basement membrane matrix", Cell and Tissue Research, 2013, vol. 354, pp. 897-902, cited in ISR (6 pages).

(Continued)

*Primary Examiner* — Marcia S Noble
(74) *Attorney, Agent, or Firm* — Westerman, Hattori, Daniels and Adrian, LLP

(57) ABSTRACT

An immortalized sweat gland myoepithelial cell which expresses α-SMA and pan-cytokeratin and has a sphere forming ability after subculture at least 5 times. A method for producing immortalized sweat gland myoepithelial said method comprising: while culturing a cell structure, wherein sweat gland myoepithelial cells are exposed on a surface, in a state of being suspended in a medium, transferring an immortalizing gene into the cells; and then culturing the transgenic structure thus obtained in a state of being suspended in the medium to thereby obtain immortalized sweat gland myoepithelial cells.

2 Claims, 4 Drawing Sheets

(56) References Cited

OTHER PUBLICATIONS

International Search Report dated Oct. 30, 2018, issued in counterpart International Application No. PCT/JP2018/029594 (2 pages).
Notice of Reasons for Refusal dated May 7, 2019, issued in counterpart JP Patent Application No. 2018-567964, w/English translation (8 pages).
Decision to Grant a Patent dated Jul. 23, 2019, issued in counterpart JP Patent Application No. 2018-567964, w/English translation (5 pages).
Extended European Search Report dated Mar. 26, 2021, issued in counterpart European Application No. 18844352.7 (in English; 8 pages).

* cited by examiner

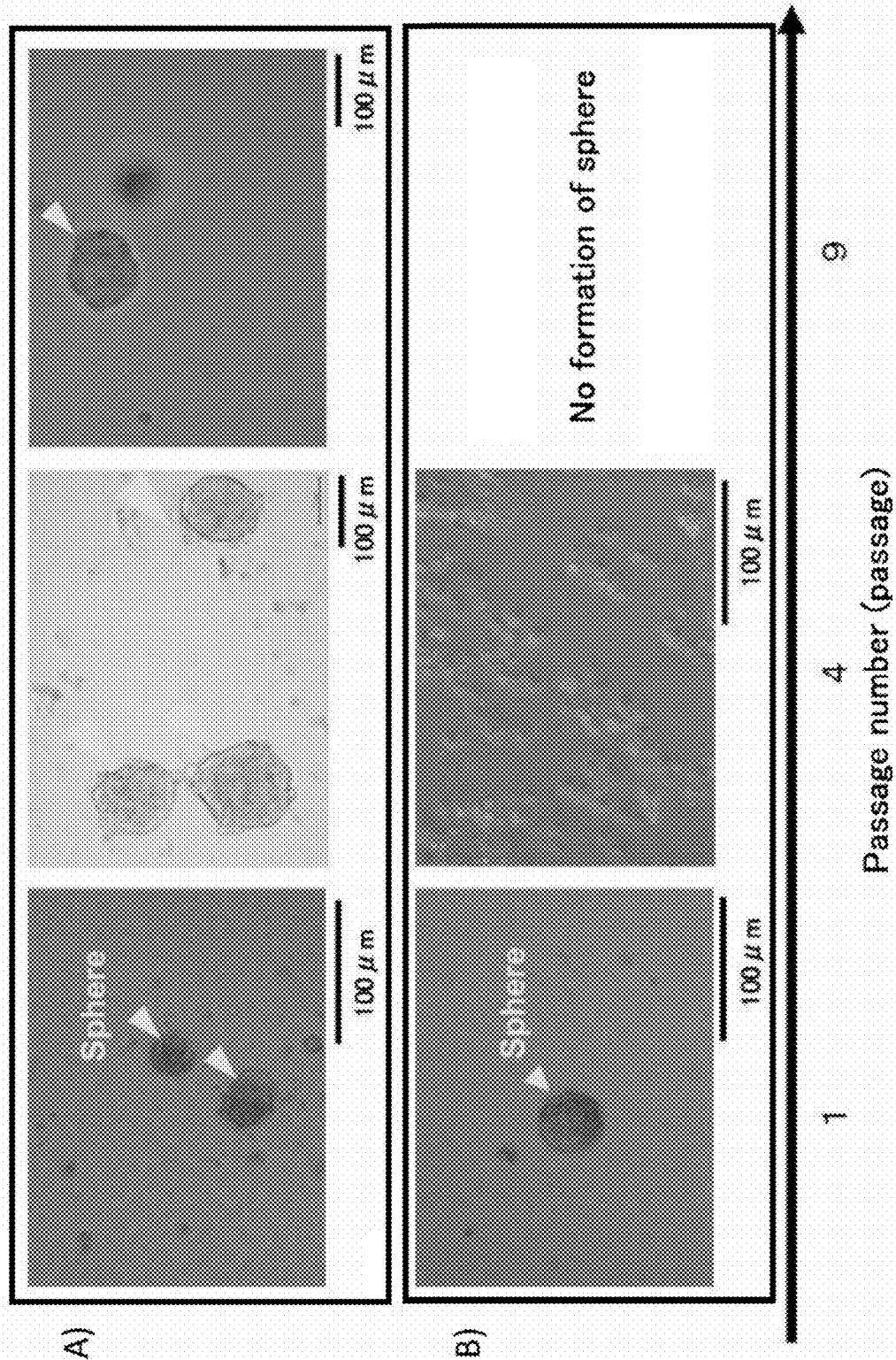

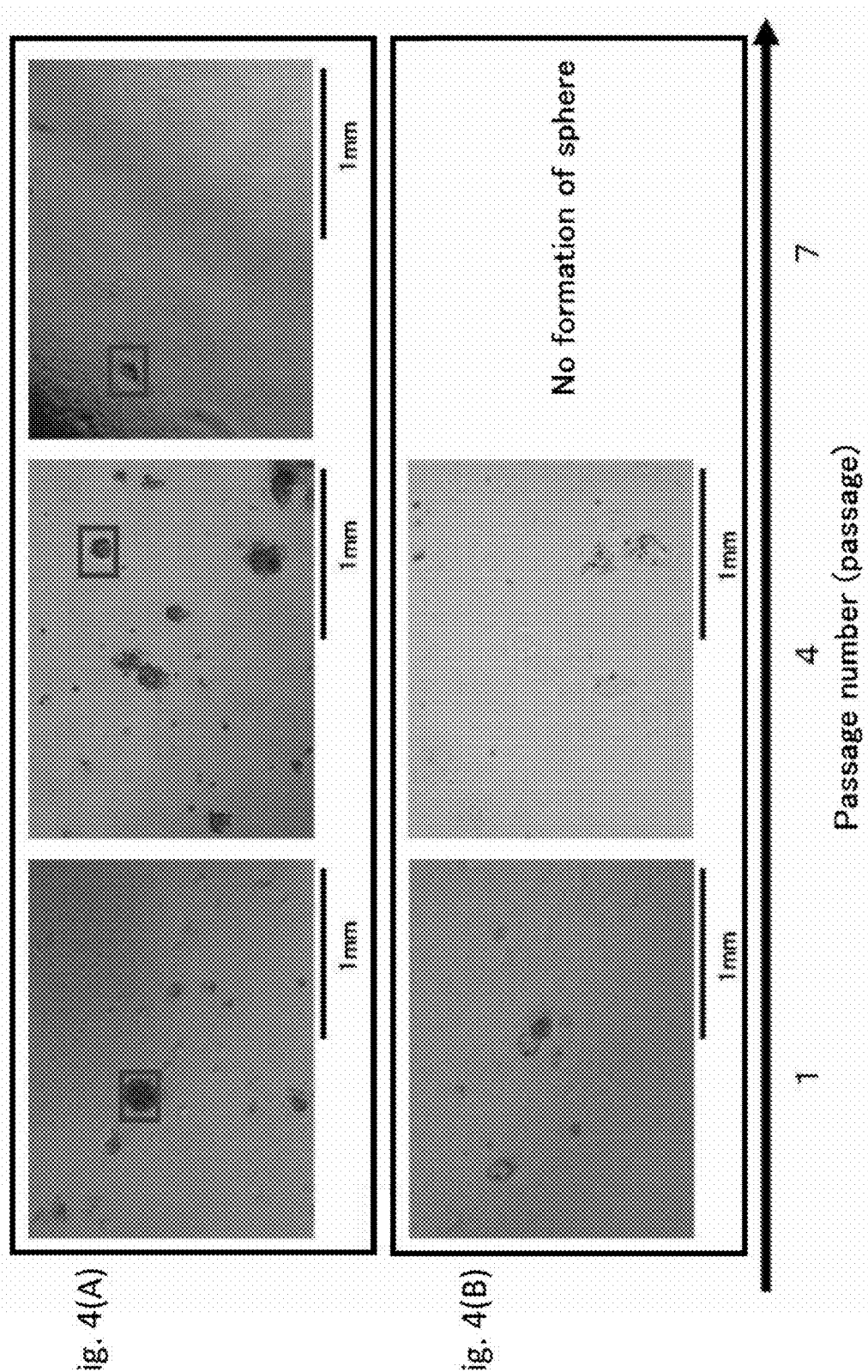

IMMORTALIZED SWEAT GLAND MYOEPITHELIAL CELL

TECHNICAL FIELD

The present invention relates to an immortalized sweat gland myoepithelial cell. More specifically, the present invention relates to an immortalized sweat gland myoepithelial cell and a method for producing the same, which are useful for development of an external preparation such as an antiperspirant or a deodorant agent, an agent for improving a function of a sweat gland, and the like.

BACKGROUND ART

In some cases, dysfunction and hyperfunction of a sweat gland may cause a disease such as heat stroke, skin stickiness, discomfort and the like. A sweat gland myoepithelial cell is one of sweat gland-constituting cells. The sweat gland myoepithelial cell is involved in movement of a sweat gland during perspiration. In addition, it has been reported by the present inventors that the sweat gland myoepithelial cell is a stem cell in a sweat gland (see, for example, Non-patent Literature 1). Accordingly, it is considered that the sweat gland myoepithelial cell is used for evaluation of the function of a sweat gland, and the like, in order to develop a means for improving the dysfunction and hyperfunction of a sweat gland.

However, a sweat gland myoepithelial cell isolated from a sweat gland has a disadvantage such that the sweat gland myoepithelial cell isolated from a sweat gland is poor in availability and handleability, since the amount of sweat gland myoepithelial cells that present in a sweat gland is small, and the passage number of enabling subculture is also low. Accordingly, it has been desired to immortalize a sweat gland myoepithelial cell, thereby imparting potential to proliferate cells for a long period of time to a sweat gland myoepithelial cell.

As a method for immortalizing a sweat gland cell, a method including a step of infecting with simian virus 40 (hereinafter referred to as "SV40") a sweat gland cell cultured in a state where the sweat gland cell is adhered to a culture container has been reported (see, for example, Non-patent Literature 2). However, the method has a disadvantage in that it is difficult to obtain an immortalized sweat gland myoepithelial cell having the same function as that of the sweat gland cell and the same property as that of the sweat gland cell in a living body, because a sweat gland cell is cultured in the environment different from living body environment. On the other hand, it is considered that a sweat gland cell is cultured in a suspended state in a medium. At present, however, the present inventors have not found a document specifically disclosing a technique for enabling to introduce a foreign gene into a sweat gland cell in a suspended state.

PRIOR ART DOCUMENTS

Non-Patent Literatures

Non-patent Literature 1: Ryuichiro Kurata et al., "Isolation and Characterization of Sweat Gland Myoepithelial Cells from Human Skin", Cell Structure and Function, Vol. 39, published in 2014, pp. 101-112

Non-patent Literature 2: CATHERINE M. LEE et al., "NCL-SG3: a human eccrine sweat gland cell line that retains the capacity for transepithelial ion transport", Journal of Cell Science, Vol. 92, published in 1989, pp. 241-249

SUMMARY OF THE INVENTION

Problems to be Solved by the Invention

The present invention has been accomplished in view of the above-mentioned prior art. An object of the present invention is to provide an immortalized sweat gland myoepithelial cell which has the same function as that of the sweat gland myoepithelial cell and the same property as that of the sweat gland myoepithelial cell in a living body, which can propagate cells each having the above function and the above property, for a long period of time, and a method for producing an immortalized sweat gland myoepithelial cell, which can produce the immortalized sweat gland myoepithelial cell with high production efficiency.

Means for Solving the Problems

The present invention relates to:
(1) an immortalized sweat gland myoepithelial cell characterized in that the immortalized sweat gland myoepithelial cell expresses α-smooth muscle actin and pan-cytokeratin and has sphere-forming ability after at least 5 passages;
(2) the immortalized sweat gland myoepithelial cell according to the item (1), wherein the immortalized sweat gland myoepithelial cell further expresses ATP1a1;
(3) a method for producing an immortalized sweat gland myoepithelial cell, including the steps of:
(I) introducing an immortalizing gene into a sweat gland myoepithelial cell while culturing in a suspended state in a medium, a cell structure in which the sweat gland myoepithelial cell included in the cell structure is exposed on a surface of the cell structure, to obtain a transgenic; and
(II) culturing the transgenic obtained in the step (I) in a suspended state in a medium, to obtain an immortalized sweat gland myoepithelial cell;
(4) the method for producing an immortalized sweat gland myoepithelial cell according to the item (3), wherein an immortalizing gene is introduced into the sweat gland myoepithelial cell through a viral vector in the step (I):
(5) the method for producing an immortalized sweat gland myoepithelial cell according to the item (3) or (4), further including a step of removing all or a part of collagen fibers from a collected skin tissue, to obtain a sweat gland-containing tissue, before carrying out the step (I), wherein the sweat gland-containing tissue is used as the cell structure in the step (I); and
(6) the method for producing an immortalized sweat gland myoepithelial cell according to the item (3) or (4), further including a step of culturing a sweat gland cell in a suspended state in a medium to form a sphere in which a sweat gland myoepithelial cell included in the sphere is exposed on a surface of the sphere, before carrying out the step (I), wherein the sphere is used as the cell structure in the step (I).

Effects of the Invention

According to the immortalized sweat gland myoepithelial cell of the present invention, there are exhibited excellent effects such that the immortalized sweat gland myoepithelial cell has the same function as that of the sweat gland myoepithelial cell and the same property as that of the sweat gland myoepithelial cell in a living body, and propagate cells each having the above function and the above property, for a long period of time. In addition, according to the method for producing an immortalized sweat gland myoepithelial cell of the present invention, there are exhibited excellent effects such that the immortalized sweat gland myoepithelial cell of the present invention can be produced with high production efficiency.

BRIEF DESCRIPTION OF THE DRAWINGS

FIG. 2(A) is a photograph substituted for a drawing, showing results of the relationship between sphere-forming ability and passage number of the sweat gland cell contained in the virus-infected sweat gland sphere of Example 1 examined in Experimental Example 2(1); and FIG. 2(B) is a photograph substituted for a drawing, showing results of the relationship between sphere-forming ability and passage number of the dissociated sweat gland cell of Comparative Example 1 examined in Experimental Example 2 (1).

FIG. 4(A) is a photograph substituted for a drawing, showing results of the relationship between sphere-forming ability and passage number of the sweat gland cell contained in the virus-infected tissue of Example 2 examined in Experimental Example 3; and FIG. 4(B) is a photograph substituted for a drawing, showing results of the relationship between sphere-forming ability and passage number of the dissociated sweat gland cell of Comparative Example 1 examined in Experimental Example 3.

MODE FOR CARRYING OUT THE INVENTION

Figure 1B:
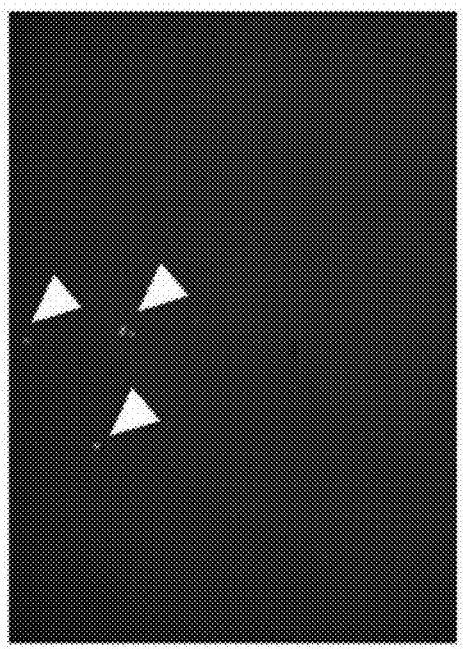
FIG. 1(B) is a photograph substituted for a drawing, showing results of fluorescence microscopy of the virus-infected sweat gland cells obtained in Reference Example 2.

As described above, the immortalized sweat gland myoepithelial cell of the present invention is characterized in that the immortalized sweat gland myoepithelial cell expresses α-smooth muscle actin and pan-cytokeratin, and has sphere-forming ability after at least 5 passages.

In the present specification, "immortalized" shows that a cell has sphere-forming ability after at least 5 passages. In addition, a "sweat gland myoepithelial cell isolated from a sweat gland" refers to a primary-cultured sweat gland myoepithelial cell isolated from a sweat gland (hereinafter also referred to as a "primary sweat gland myoepithelial cell").

Alpha-smooth muscle actin and pan-cytokeratin are sweat gland myoepithelial cell markers in a living body. Alpha-smooth muscle actin is involved in expression of a function of a sweat gland myoepithelial cell, such that contraction of a sweat gland is caused. In addition, pan-cytokeratin forms a cytoskeleton of a sweat gland myoepithelial cell. Since the immortalized sweat gland myoepithelial cell of the present invention expresses α-smooth muscle actin and pan-cytokeratin, the immortalized sweat gland myoepithelial cell of the present invention has the same function as that of the sweat gland myoepithelial cell and the same property as that of the sweat gland myoepithelial cell in a living body. Furthermore, since the immortalized sweat gland myoepithelial cell of the present invention has the sphere-forming ability after at least 5 passages, the immortalized sweat gland myoepithelial cell of the present invention can propagate cells each having the same function as that of the sweat gland myoepithelial cell and the same property as that of the sweat gland myoepithelial cell in a living body, for a long period of time, as compared with the primary sweat gland myoepithelial cell.

The primary sweat gland myoepithelial cell lose sphere-forming ability before the fourth passage. In contrast, the immortalized sweat gland myoepithelial cell of the present invention has sphere-forming ability even after at least 5 passages, preferably 7 passages or more, more preferably 9 passages or more, even more preferably 18 passages or more, furthermore preferably 100 passages or more. Accordingly, the immortalized sweat gland myoepithelial cell of the present invention maintains cell proliferative capacity for a longer period of time as compared with the primary sweat gland myoepithelial cell.

The "same function as that of the sweat gland myoepithelial cell in a living body" includes, for example, contraction movement of a sweat gland during perspiration and the like, and the present invention is not limited only to those exemplified ones. The "same property as that of a sweat gland myoepithelial cell in a living body" includes, for example, differentiation potential into a sweat gland lumen cell, self-renewal ability, positive expression of α-smooth muscle actin, positive expression of pan-cytokeratin, positive expression of sodium/potassium. ATPase α subunit (ATP1a1) and the like, and the present invention is not limited only to those exemplified ones.

It is preferred that the immortalized sweat gland myoepithelial cell of the present invention further expresses ATP1a1. Since ATP1a1 is not expressed in a myoepithelial cell derived from an organ other than a sweat gland (for example, a myoepithelial cell derived from a mammary gland and the like), ATP1a1 is a sweat gland cell maker. Accordingly, the immortalized sweat gland myoepithelial cell of the present invention, which expresses ATP1a1, can be distinguished from a myoepithelial cell derived from an organ other than a sweat gland.

Since the immortalized sweat gland myoepithelial cell of the present invention has the same function as that of the sweat gland myoepithelial cell in a living body and the same property as that of a sweat gland myoepithelial cell in a living body, it is expected that the immortalized sweat gland myoepithelial cell of the present invention is used, for example, for an evaluation method of a differentiation-regulating effect for a sweat gland myoepithelial cell, which is exhibited by a test substance. The evaluation method includes, for example, the steps of:

(A) culturing the immortalized sweat gland myoepithelial cell of the present invention in a suspended state in a medium in the absence of a test substance, to obtain a cell-cultured product;

(B) culturing the immortalized sweat gland myoepithelial cell of the present invention in a suspended state in a medium in the presence of a test substance, to obtain a cell-cultured product; and (C) examining an expression profile of a differentiation marker in the cell-cultured product (A) obtained in the step (A) and an expression profile of a differentiation marker in the cell-cultured product (B) obtained in the step (B), to evaluate a differentiation-regulating effect for a sweat gland myoepithelial cell, which is exhibited by the test substance on the basis of difference between an expression profile of the differentiation marker in the cell-cultured product (A) and an expression profile of the differentiation marker in the cell-cultured product (B).

When it is confirmed by the present evaluation method that the test substance has a differentiation-enhancing effect for a sweat gland myoepithelial cell, it is expected that the test substance is used for improvement of a state caused by hyperfunction of a sweat gland myoepithelial cell. In addition, when it is confirmed by the present evaluation method that the test substance has a differentiation-inhibiting effect for a sweat gland myoepithelial cell, it is expected that the test substance is used for improvement of a state caused by dysfunction of a sweat gland myoepithelial cell.

The immortalized sweat gland myoepithelial cell of the present invention can be produced by, for example, introducing an immortalizing gene into a sweat gland myoepithelial cell while culturing in a suspended state in a medium, a cell structure in which a sweat gland myoepithelial cell included in the cell structure is exposed on the surface of the cell structure.

The method for producing an immortalized sweat gland myoepithelial cell of the present invention is characterized in that the method includes the steps of:
(I) introducing an immortalizing gene into a sweat gland myoepithelial cell while culturing in a suspended state in a medium, a cell structure in which the sweat gland myoepithelial cell included in the cell structure is exposed on the surface of the cell structure, to obtain a transgenic; and
(II) culturing the transgenic obtained in the step (I) in a suspended state in a medium, to obtain an immortalized sweat gland myoepithelial cell (hereinafter also referred to as "the method of the present invention").

According to the method of the present invention, since a procedure including the steps of introducing an immortalizing gene into a sweat gland myoepithelial cell while culturing in a suspended state in a medium, a cell structure in which the sweat gland myoepithelial cell included in the cell structure is exposed on the surface of the cell structure is adopted, an immortalizing gene can be introduced into a sweat gland myoepithelial cell with high transfer efficiency. Accordingly, according to the method of the present, invention, an immortalized sweat gland myoepithelial cell can be produced with high production efficiency.

In the step (I), an immortalizing gene is introduced into a sweat gland myoepithelial cell, while culturing in a suspended state in a medium, a cell structure in which the sweat gland myoepithelial cell included in the cell structure is exposed on the surface of the cell structure, to obtain a transgenic.

The cell structure can contain other sweat gland cells and the like, as long as a sweat gland my epithelial cell is exposed oh a surface of the cell structure. Other sweat gland cells include, for example, a sweat gland lumen cell, a sweat gland secretory cell and the like, and the present invention is not limited only to those exemplified ones. The cell structure includes, for example, a sweat gland-containing tissue in which a sweat gland myoepithelial cell included in the tissue is exposed on the surface of the tissue, a sphere in which a sweat gland myoepithelial cell included in the sphere is exposed on the surface of the sphere and the like, and the present invention is not limited only to those exemplified ones.

The sweat gland-containing tissue is a tissue of a portion containing a sweat gland in a skin tissue. An outer layer of the sweat gland contained in the sweat gland-containing tissue is covered with sweat gland myoepithelial cells. In addition, in a sweat gland, a sweat gland cell present in an inside of the sweat gland is more differentiated than a sweat gland cell present in an outside. The sweat gland-containing tissue can be separated by, for example, removing all or a part of collagen fibers from a collected skin tissue. When a sweat gland-containing tissue is used as the cell structure, the method of the present invention can further include a step of removing all or a part of collagen fibers from a collected skin tissue, to obtain a sweat gland-containing tissue in which a sweat gland myoepithelial cell is exposed on the surface of the tissue, before carrying out the step (I).

The method for producing a sweat gland-containing tissue includes, for example, a method including the steps of:
(a1) separating a tissue piece containing a sweat gland from a collected skin tissue; and
(a2) removing collagen fibers and the like from the tissue piece obtained in the step (a1), to obtain a sweat gland-containing tissue in which a sweat gland myoepithelial cell included in the tissue is exposed on the surface of the tissue and the like, and the present invention is not limited only to those exemplified ones.

The collected skin tissue includes, for example, a living skin tissue obtained from excess skin removed during a surgical operation and the like, and the present invention is not limited only to those exemplified ones. It is preferred that the collected skin tissue is a fresh tissue from the viewpoint of more excellently maintaining a function and a property of a sweat gland myoepithelial cell in a living body. When the collected skin tissue is a tissue refrigerated in cold storage, it is preferred that the tissue has been excised within 48 hours from the viewpoint of more excellently maintaining a function and a property of a sweat gland myoepithelial cell in a living body. In the present specification, the "living skin tissue" refers to a skin tissue exhibiting the same biological activity as an inherent biological activity and the same movement as an inherent movement in a living body. The source of the skin tissue includes, for example, a human and the like, and the present invention is not limited only to those exemplified ones.

In the step (a1), the tissue piece containing a sweat gland is separated from a collected skin tissue. Since the tissue piece containing a sweat gland can be easily separated while visually confirming the sweat gland in the step (a1), it is preferred to stain the skin tissue with a staining reagent such as neutral red to visualize the sweat gland. When the skin tissue is stained, it is preferred to wash the tissue piece separated from the skin tissue from the viewpoint of reducing influence of a staining reagent on a sweat gland and reducing contamination with microorganism and the like.

Next, in the step (a2), collagenous fibers are removed from the tissue piece obtained in the step (a1), to obtain a sweat gland-containing tissue in which a sweat gland myoepithelial cell included in the tissue is exposed on the surface of the tissue. In the step (a2), for example, the collagenous fibers can be removed from the tissue piece by using an enzyme such as dispase or collagenase, a physical excision means and the like. In the step (a2), it is preferred to further remove a hair follicle, a sebaceous gland and the like from the tissue piece, from the viewpoint of preventing contamination with other epidermal appendages.

The sphere is an aggregate of sweat gland cells. The sphere has a surface layer including sweat gland myoepithelial cells. In the sphere, a sweat gland cell present in an inside of the sphere is more differentiated than a sweat gland cell present in an outside of the sphere. The sphere can be produced by, for example, culturing a sweat gland cell in a suspended state in a medium, and the like. When the sphere is used as the cell structure, the method of the present invention can further include a step of culturing a sweat gland cell in a suspended state in a medium before carrying out step (I), to form a sphere in which a sweat gland myoepithelial cell included in the sphere is exposed on the surface of the sphere.

The method for producing a sphere includes, for example, a method including the steps of:
(b1) separating a tissue piece containing a sweat gland from a collected skin tissue;
(b2) obtaining a sweat gland cell in a dissociated state from the tissue piece obtained in the step (b1); and
(b3) culturing in a suspended state in a medium, a sweat gland cell obtained in the step (b2), to form a sphere in which a sweat gland myoepithelial cell included in the sphere is exposed on the surface of the sphere,
and the like, and the present invention is not limited only to those exemplified ones.

In the step (b1) a tissue piece containing a sweat gland is separated from a collected skin tissue. The tissue piece in the step (b1) can be collected in the same manner as in the collection of tissue piece in the step (a1) of the method for producing the sweat gland-containing tissue.

Next, in the step (b2), a sweat gland cell in a dissociated state is obtained from the tissue piece obtained in the step (b1). In the step (b2), the sweat gland cell in a dissociated state can be obtained by, for example, treating a tissue piece with a cell dissociation reagent, to dissociate a sweat gland cell from the tissue piece, and the like. The cell dissociation reagent includes, for example, an enzyme such as thermolysin, dispase, collagenase or trypsin, and the like, and the present invention is not limited only to those exemplified ones.

Next, in the step (b3), the sweat gland cell in a dissociated state, which is obtained in the step (b2), is cultured in a state of suspending the sweat gland cell in a sphere formation medium, to form a sphere in which a sweat gland myoepithelial cell included in the sphere is exposed on the surface of the sphere. The sphere formation medium includes, for example, a medium containing epidermal growth factor, basic fibroblast growth factor, an artificial basement membrane matrix for cell culture and a serum-free medium and the like, and the present invention is not limited only to those exemplified ones. When the sphere formation medium is a medium containing an epidermal growth factor, the content of the epidermal growth factor in the sphere formation medium cannot be absolutely determined, because the content of the epidermal growth factor varies depending on the kind of the source of the skin tissue and the like. It is therefore preferred to appropriately determine the content in accordance with the kind of the source of the skin tissue and the like. When the source of the skin tissue is a human, the content of the epidermal growth factor in the sphere formation medium is usually preferably 0.01 ng/mL or more, and more preferably 1 ng/mL or more, from the viewpoint of moderately propagating and moderately differentiating the cells, and preferably 1 µg/mL or less, and more preferably 100 ng/mL or less, from the viewpoint of inhibiting excess growth and excess differentiation of the cells. When the sphere formation medium is a medium containing basic fibroblast growth factor, the content of basic fibroblast growth factor in the sphere formation medium cannot be absolutely determined because the content of basic fibroblast growth factor varies depending on the kind of the source of the skin tissue and the like. It is therefore preferred to appropriately determine the content of basic fibroblast growth factor in the sphere formation medium in accordance with the kind of the source of the skin tissue and the like. When the source of the skin tissue is a human, the content of the basic fibroblast growth factor in the sphere formation medium is usually preferably 0.01 ng/mL or more, and more preferably 1 ng/mL or more, from the viewpoint of moderately propagating the cells and inhibiting excess differentiation of the cells, and preferably 1 µg/mL or less, and more preferably 100 ng/mL or less, from the viewpoint of inhibiting excess growth and excess differentiation of the cells. The serum-free medium includes, for example, a product manufactured by STEMCELL Technologies under the trade name of Compete MammoCult Human Medium, a product manufactured by Thermo Fisher Scientific K. K. under the trade name of Gibco (registered trademark) Keratinocyte-SFM and the like, and the present invention is not limited only to those exemplified ones.

The culture conditions cannot be absolutely determined because culture conditions for the sweat gland cell vary depending on the kind of the source of the skin tissue and the like. It is therefore preferred to appropriately determine the culture conditions in accordance with the kind of the source of the skin tissue and the like. The culture conditions for the sweat gland cell include, for example, culture temperature, culture period, pH of the medium, carbon dioxide concentration in a culture atmosphere and the like. When the source of the skin tissue is a human, the culture temperature is preferably 35° C. or higher, and more preferably 36.5° C. or higher, from the viewpoint of favorably maintaining a function and a property of a sweat gland myoepithelial cell in a living body, and preferably 38° C. or lower, and more preferably 37.5° C. or lower, from the same viewpoint as in the above of maintaining a function and a property of a sweat gland myoepithelial cell in a living body. More specifically, the culture temperature is usually preferably 35 to 38° C., and more preferably 36.5 to 37.5° C., from the viewpoint of more excellently maintaining a function and a property of a sweat gland myoepithelial cell in a living body. In addition, when the source of the skin tissue is a human, the culture period cannot be absolutely determined because the culture period varies depending on the culture temperature and the like. It is therefore preferred to appropriately determine the culture period in accordance with the culture temperature and the like. The culture period is preferably 60 hours or more, and more preferably 144 hours or more, from the viewpoint of favorably maintaining a function and a property of a sweat gland myoepithelial cell in a living body, and preferably 672 hours or less, and more preferably 168 hours or less, from the same viewpoint as in the above of more excellently maintaining a function and a property of a sweat gland myoepithelial cell in a living body. More specifically, the culture period is usually preferably 60 to 672 hours, and more preferably 144 to 168 hours, from the viewpoint of more excellently maintaining a function and a property of a sweat gland myoepithelial cell in a living body. Furthermore, When the source of the skin tissue is a human, pH of the medium is preferably 6.8 or mere, and more preferably 7.0 or more, from the viewpoint of maintaining a function and a property of the sweat gland cell in a living body, and preferably 7.6 or less, and more preferably 7.4 or less, from the same viewpoint as in the above of more excellently maintaining a function and a property of a sweat gland myoepithelial cell in a living body. More specifically, the pH is usually preferably 6.8 to 7.6, and more preferably 7.0 to 7.4, from the viewpoint of more excellently maintaining a function and a property of a sweat gland myoepithelial cell in a living body. The carbon dioxide concentration in the culture atmosphere is preferably 4% by volume more, and more preferably 5% by volume or more, from the viewpoint of more excellently maintaining a function and a property of a sweat gland myoepithelial cell in a living body, and preferably 10% by volume or less, and more preferably 7% by volume or less, from the same viewpoint as in the above of more excellently maintaining a function and a property of a sweat gland myoepithelial cell in a living body. More specifically, the carbon dioxide concentration is usually preferably 4 to 10% by volume, and more preferably 5 to 7% by volume, from the viewpoint of more excellently maintaining a function and a property of a sweat gland myoepithelial cell in a living body. The "state of suspending the sweat gland cell in a medium" is not particularly limited as long as the sweat gland cell does not contact with a wall surface of a culture container used for culturing the sweat gland cell. The culture container can be a container containing a substance for inhibiting adhesion of a sweat gland cell on the inner surface of the container.

In the step (I), an immortalizing gene is introduced into a sweat gland myoepithelial cell while culturing the cell structure in a state of suspending the cell structure in a medium. The "state of suspending the cell structure in a medium" is not specifically limited as long as the cell structure does not contact with an inner surface of a container used for culturing the cell structure. The container used for culturing the cell structure can be a container containing a substance for inhibiting adhesion of the cell structure on the inner surface of the container. The medium for culturing the cell structure in a suspended state (hereinafter also referred to as "a medium for suspension culture") can be a medium in which a content of a component for inhibiting gene transfer such as serum is low, or a medium not containing the component, as long as the medium contains a nutrient component for maintaining the sweat gland myoepithelial cell alive. The medium for suspension culture can be a medium prepared by supplementing the low-serum medium or the serum-free medium with a nutrient component, or an easily commercially available medium. The nutrient component includes, for example, an amino acid, a vitamin, an inorganic salt, a saccharide, a cell growth factor (for example, epidermal growth factor, basic fibroblast growth factor, hydrocortisone-21-hemisuccinate and the like) and the like, and the present invention is not limited only to those exemplified ones. The content of the nutrient component in the medium for suspension culture cannot be absolutely determined because the content of the nutrient component varies depending on the kind of the low-serum medium or the serum-free medium, the kind of the nutrient components and the like. It is therefore preferred to appropriately control the content of the nutrient component in the medium for suspension culture in accordance with on the kind of the low-serum medium or the serum-free medium, the kind of the nutrient components, and the like. These nutrient components can be used alone, or in combination of two or more kinds of nutrient components. The serum-free median includes, for example, a product manufactured by STEMCELL Technologies under the trade name of Complete MammoCult Human Medium, a product manufactured by Thermo Fisher Scientific K. K. under the trade name of Gibco (registered trademark) Keratinocyte-SFM, a product manufactured by Thermo Fisher Scientific K. K. under the trade name of Opti-MEM (registered trademark) I Reduced Serum Medium and the like, and the present invention is not limited only to those exemplified ones. As the low-serum medium, a medium prepared by adding serum to the serum-free medium can be used. The serum concentration of the low-serum medium is preferably 0.01% by volume or more, and more preferably 0.1% by volume or more, from the viewpoint of more excellently maintaining a function and a property of a sweat gland myoepithelial cell in a living body, and preferably 0.5% by volume or less, and more preferably 0.1% by volume or less, from the same viewpoint as in the above of more excellently maintaining a function and a property of a sweat gland myoepithelial cell in a living body. More specifically, the serum concentration is preferably 0.1 to 0.5% by volume, and more preferably 0.01 to 0.1% by volume.

The method for introducing an immortalizing gene into a sweat gland myoepithelial cell includes, for example, a method using a viral vector, a transfection method and the like, and the present invention is not limited only to those exemplified ones. Among these methods, the method using a viral vector is preferable, since high gene transfer efficiency can be achieved with simple operations. Accordingly, it is preferred to introduce an immortalized gene into the sweat gland myoepithelial cell through a viral vector in the step (I).

The viral vector includes, for example, a lentiviral vector, a retroviral vector and the like, and the present invention is not limited only to those exemplified ones. Among these viral vectors, the lentiviral vector is preferable, since the lentiviral vector exhibits high gene transfer efficiency to a sweat gland myoepithelial cell, and enables to perform stable introduction of an immortalizing gene. The immortalizing gene includes, for example, human telomerase reverse transcriptase (hTERT) gene, SV40t (small t) antigen gene, SV40T (large T) antigen gene, c-myc gene, papillomavirus E6 gene, papillomavirus E7 gene and the like, and the present invention is not limited only to those exemplified ones. These immortalizing genes can be used alone, or in combination of two or more kinds of the immortalizing genes. Among these immortalizing genes, it is preferable to use hTERT gene, SV40t antigen gene and SV40T antigen gene in combination, since high gene transfer efficiency to a sweat gland myoepithelial cell can be achieved.

In the step (I), when the immortalizing gene is introduced into the sweat gland myoepithelial cell by the method using a viral vector, the immortalizing gene can be introduced into the sweat gland myoepithelial cell by infecting the cell structure with a recombinant viral particle in which a viral vector carrying an immortalizing gene is packaged, Wherein the cell structure is a cell structure in which the sweat gland myoepithelial cell included in the cell structure is exposed on the surface of the cell structure. The recombinant viral particle can be prepared by, for example, cotransfecting a recombinant viral vector obtained by introducing an immortalizing gene into a viral vector and a vector carrying a gene necessary for packaging of the virus into a cell for cotransfection, to obtain a recombinant viral particle; and collecting the resulting recombinant viral particle. The recombinant viral particle can be an easily commercially available recombinant viral particle. An immortalizing gene can be introduced into the cell structure by contacting the cell structure with the recombinant, viral particle in the presence of a gene transfer adjuvant, to infect the cell structure with the recombinant viral particle. The cell for cotransfection includes, for example, 293T cell and the like, and the present invention is not limited only to those exemplified ones. The gene transfer adjuvant includes, for example, polybrene, protamine and the like, and the present invention is not limited only to those exemplified ones.

The method for contacting a cell structure with a recombinant viral particle includes, for example, a method including a step of adding the recombinant viral particle to a viral infection medium containing the cell structure in a suspended state, a method including a step of mixing the cell structure with a viral infection medium containing the recombinant viral particle and the like, and the present invention is not limited only to those exemplified ones. The viral infection medium includes, for example, a medium prepared by supplementing the serum-free medium with hydrocortisone-21-hemisuccinate, recombinant human epidermal growth factor, recombinant human basic fibroblast growth factor, glutamic acid, a non-essential amino acid and the like, an easily commercially available medium and the like, and the present invention is not limited only to those exemplified ones.

When the sweat gland-containing tissue in which a sweat gland myoepithelial cell included in the tissue is exposed on the surface of the tissue is used as the cell structure, the number of sweat glands contained in the sweat gland-containing tissue per 100 μL of a mixture of the sweat gland-containing tissue and the recombinant viral particle is preferably 1 or more, and more preferably 4 or more, from the viewpoint of improving gene transfer efficiency to improve production efficiency, and preferably 20 or less, and more preferably 10 or less, from the same viewpoint as in the above of improving gene transfer efficiency to improve production efficiency. More specifically, the number of sweat glands contained in the sweat gland-containing tissue per 100 μL of the mixture is preferably 1 to 20, and more preferably 4 to 10. In addition, when the sweat gland-containing tissue is used as the cell structure, the ratio of the number of infected viral particles to the number of sweat glands (the number of infected viral particles/the number of sweat glands) is preferably $1 \times 10^2$ to $1 \times 10^{10}$.

When the sphere in which a sweat gland myoepithelial cell included in the sphere is exposed on the surface of the sphere is used as the cell structure, the number of the sphere per 100 μL of a mixture of the sphere and the recombinant viral particle is preferably 1 or more, and more preferably 4 or more, from the viewpoint of improving gene transfer efficiency to improve production efficiency, and preferably 20 or less, and more preferably 10 or less, from the same viewpoint as in the above of improving gene transfer efficiency to improve production efficiency. More specifically, the number of the spheres contained per 100 μL of the mixture is preferably 1 to 20, and more preferably 4 to 10. In addition, when the sphere is used as the cell structure, the ratio of the number of infected viral particles to the number of spheres (the number of infected viral particles/the number of spheres) is preferably $1 \times 10^2$ to $1 \times 10^{10}$.

Next, in the step (II), the transgenic obtained in the step (I) is cultured in a state of suspending the transgenic in a medium, to obtain an immortalized sweat gland myoepithelial cell.

The medium used in the step (II) can be the same as the medium for suspension culture used in the step (I). The culture conditions of the transgenic in the step (II) can be the same as the culture conditions for the sweat gland cell in the method for producing a sphere.

When the sweat gland-containing tissue in which a sweat gland myoepithelial cell included in the tissue is exposed on the surface of the tissue is used as the cell structure, since the transgenic obtained in the step (I) contains a tissue other than a sweat gland, and the like, there can be further carried out a step of isolating an immortalized sweat gland myoepithelial cell from the transgenic. The immortalized sweat gland myoepithelial cell can be isolated from the transgenic by, for example, treatment of the transgenic with a cell dissociation reagent, a dynamic stimulus of the transgenic, combination use of a cell dissociation reagent and a dynamic stimulus, and the like. The cell dissociation reagent is the same as the cell dissociation reagent used in the step (b2) of the method for producing a sphere. The dynamic stimulus includes, for example, a stimulus by pipetting and the like, and the present invention is not limited only to those exemplified ones.

When the transgenic contains a cell other than an immortalized sweat gland myoepithelial cell, the method of the present invention can further include a step of isolating an immortalized sweat gland myoepithelial cell after carrying out the step (II). The method for isolating an immortalized sweat gland myoepithelial cell includes, for example, cell sorting in which a sweat gland myoepithelial cell specific marker is used, and the like, and the present invention is not limited only to those exemplified ones.

The immortalized sweat gland myoepithelial cell obtained by the method of the present invention can be identified by examining characteristics of a sweat gland myoepithelial cell (i) to (iii):

(i) positive expression of α-smooth muscle actin:
(ii) positive expression of pan cytokeratin and positive expression of ATP1a1; and
(iii) possession of sphere-forming ability after 5 passages.

Presence or absence of expression of each of α-smooth muscle actin, pan-cytokeratin and ATP1a1 can be confirmed by, for example, immunofluorescence staining method, real-time RT-PCR method and the like. The sphere-forming ability can be confirmed by the same method as the above-mentioned method for producing a sphere.

As explained above, the immortalized sweat gland myoepithelial cell of the present invention has the same function as that of the sweat gland myoepithelial cell and the same property as that of a sweat gland myoepithelial cell in a living body, and can propagate cells having the above function and the above property for a long period of time. In addition, according to the method for producing an immortalized sweat gland myoepithelial cell of the present invention, the immortalized sweat gland myoepithelial cell of the present invention can be obtained with high production efficiency. Accordingly, it is expected that the immortalized sweat gland myoepithelial cell of the present invention and the method for producing an immortalized sweat gland myoepithelial cell of the present invention are used for development of an external preparation such as an antiperspirant and a deodorant agent, an agent for improving the function of a sweat gland and the like.

EXAMPLES

The present invention will be more specifically explained in accordance with the following working examples, but the present invention is not limited to the examples. Hereafter, meanings of each abbreviation and each term are as follows:

Explanation of Abbreviations and Terms

EDTA: ethylenediaminetetraacetic acid
FBS: fetal bovine serum
GAPDH: glyceraldehyde-3-phosphate dehydrogenase
GFP: green fluorescent protein
GFP recombinant virus: recombinant lentivirus carrying GFP gene
hTERT recombinant virus: recombinant lentivirus carrying hTERT gene PBS: phosphate-buffered saline SV40Tt recombinant virus: recombinant lentivirus carrying SV40t antigen gene and SV40T antigen gene α-SMA: α-smooth muscle actin Production Example 1

Hydrocortisone-21-hemisuccinate, recombinant human epidermal growth factor, recombinant human basic fibroblast growth factor, heparin and penicillin/streptomycin liquid mixture [penicillin concentration: 10,000 units/mL, streptomycin concentration: 10,000 μg/mL] were added to a basal medium [manufacture by STEMCELL Technologies under the trade name of Complete MammoCult Human Medium] so as to have a concentration of 10.5 μg/mL (hydrocortisone-21-hemisuccinate), a concentration of 10 ng/mL (recombinant human epidermal growth factor), a concentration of 10 ng/mL (recombinant human basic fibroblast growth factor), a concentration of 4 μg/mL (heparin) and a concentration of 100 μg/mL (penicillin/streptomycin liquid mixture), to obtain a medium (I).

Production Example 2

Hydrocortisone-21-hemisuccinate, recombinant human epidermal growth factor, recombinant human basic fibroblast growth factor, heparin, penicillin/streptomycin liquid mixture and an artificial basement membrane matrix for cell culture [manufactured by Corning Incorporated under the trade name of Growth Factor Reduced Matrigel Matrix] were added to a basal medium [manufacture by STEMCELL Technologies under the trade name of Complete MammoCult Human Medium] so as to have a concentration of 10.5 μg/mL (hydrocortisone-21-hemisuccinate), a concentration of 10 ng/mL (recombinant human epidermal growth factor), a concentration of 10 ng/mL (recombinant human basic fibroblast growth factor), a concentration of 4 μg/mL (heparin), a concentration of 100 μg/mL (penicillin/streptomycin liquid mixture) and a concentration of 2% by volume (the artificial basement membrane matrix for cell culture), to obtain a medium (II).

Production Example 3

Hydrocortisone-21-hemisuccinate, recombinant human epidermal growth factor and recombinant human basic fibroblast growth factor were added to a basal medium [manufacture by STEMCELL Technologies under the trade name of Complete MammoCult Human Medium] so as to have a concentration of 10.5 μg/mL (hydrocortisone-21-hemisuccinate), a concentration of 10 ng/mL (recombinant human epidermal growth factor) and a concentration of 10 ng/mL (recombinant human epidermal growth factor), to obtain a medium (III). Polybrene was added to the medium (III) so as to have a concentration of 10 μg/mL, to obtain a viral infection medium.

Production Example 4

A trypsin solution [manufactured by Thermo Fisher Scientific K. K. under the trade name of 2.5% Trypsin (10×), no Phenol Red] was mixed with Dulbecco's PBS [manufactured by Thermo Fisher Scientific K. K. under the trade name of DPBS, no calcium and no magnesium], and an EDTA solution [manufactured by NIPPON GENE CO., LTD. under the trade name of 0.5 M EDTA], to obtain a 0.5% by weight trypsin-EDTA solution.

Production Example 5

Powdered dispase [manufactured by Thermo Fisher Scientific K. K. under the trade name of Dispase II, powder] was dissolved in Dulbecco's PBS [manufactured by Thermo Fisher Scientific K. K. under the trade name of DPBS, no calcium, no magnesium], to obtain 5 U/mL dispose liquid.

Reference Example 1

(1) Production of Sweat Gland Cells in Dissociated State

As a skin tissue, a skin tissue of an eyelid excised within 48 hours, which had been refrigerated in cold storage immediately after excision from a living body (a 68-year-old human), was used. The skin tissue was immersed in 10 μM Neutral Red-containing PBS, to incorporate Neutral Red into each of sweat glands in the skin tissue. Next, tissue pieces each containing a sweat gland were separated from the skin tissue by using tweezers and scissors under an optical microscope. The separated tissue pieces were gathered in aseptic PBS in a 15 mL-volume tube. The tissue pieces were washed by lightly shaking PBS containing the tissue pieces and thereafter centrifuging the PBS at 350×g and 4° C. for 5 minutes, to remove the supernatant.

Ten milliliters of the medium (I) obtained in Production Example 1 was mixed with the tissue pieces in the tube. Next, collagenase II was added to the medium (I) in the tube, so as to have a concentration of 600 U/mL. Thereafter, the tissue pieces in the tube were incubated at 37° C. in 5% by volume carbon dioxide atmosphere while rotating the tube by a rotator, to remove collagenous fibers from the tissue pieces.

After 4 hours passed from the initiation of incubation, the medium (I) and the tissue pieces from which collagenous fibers had been removed in the tube were transferred to a 10 cm-diameter dish. The tissue pieces on the dish were collected by using a pipette under an optical microscope. The collected tissue pieces were gathered in aseptic PBS in a 15 mL-volume tube. The tissue pieces were washed by lightly shaking PBS containing the tissue pieces and thereafter centrifuging the PBS at 350×g and 4° C. for 5 minutes, to remove the supernatant.

The tissue pieces after washing and 1 mL of a 0.5% by weight trypsin-EDTA solution obtained in Production Example 4 were mixed in a 15 mL-volume tube. Sweat gland cells each constituting the sweat gland were dissociated from each other by stirring the sweat glands in the tube for 3 minutes using a pipette, to obtain sweat gland cells in a dissociated state (hereinafter also referred to as "dissociated sweat gland cells").

(2) Sphere Culture

The dissociated sweat gland cells obtained in the above (1) "Production of sweat gland cells in dissociated state" were mixed with 9 mL of a 2% by weight FBS/PBS solution, to obtain liquid mixture. The resulting liquid mixture was centrifuged at 350×g and 4° C. for 5 minutes, to remove the supernatant from the liquid mixture. After adding 1 mL of the 5 U/mL dispase liquid obtained in Production Example 5 to the dissociated sweat gland cells in the tube, the dissociated sweat gland cells in the tube were stirred by using a pipette. Next, aggregated cells were removed by allowing the liquid mixture containing dissociated sweat gland cells in the tube to pass through a cell strainer [mesh size: 40 μm, manufactured by Corning Incorporated under the trade name of Falcon (registered trademark) 40 μm Cell Strainer, Blue, Sterile, Individually Packaged], to obtain a suspension liquid of dissociated sweat gland cells.

Nine milliliters of a 2% by weight FBS/PBS solution was mixed with the suspension liquid of dissociated sweat gland cells in the tube, to obtain a liquid mixture. The resulting liquid mixture was centrifuged at 350×g and 4° C. for 5 minutes to remove the supernatant from the liquid mixture, thereby obtaining a cell-containing liquid. Using a part of the cell-containing liquid and a hemocytometer, the number of cells in the cell-containing liquid was calculated. The medium (II) obtained in Production Example 2 was added to the tube so that the dissociated sweat gland cell concentration became $1\times10^3$ to $7\times10^3$ cells/mL, to obtain a liquid mixture containing dissociated sweat gland cells. The resulting liquid mixture was put into a low attachment plate [manufactured by Corning Incorporated under the trade name of Ultra-Low Attachment Plate, 24 well]. The dissociated sweat gland cells were incubated at 37° C. in 5% by volume carbon dioxide in a suspended state in the medium (II) in the plate.

When spheres were formed after starting culture (incubation), the spheres were transferred to a 15 mL-volume tube. The spheres were centrifuged at 350×g and 4° C. for 5 minutes, to remove liquid components. Next, 1 mL of a solution for cell recovery (manufactured by Corning Incorporated under the trade name of Cell Recovery Solution) was mixed with the spheres in the tube, to obtain a sphere-containing liquid. Thereafter, the tube containing the resulting sphere-containing liquid was left to stand on ice for 1 to 2 hours.

(3) Viral Infection

A GFP recombinant viral particle solution [manufactured by Applied Biological Materials Inc. under the trade name of GFP Control Lentivirus, GFP recombinant viral particle concentration: $1\times10^6$ U/mL] was concentrated in accordance with polyethylene glycol precipitation method. The resulting concentrate was diluted with the viral infection medium so that the GFP recombinant viral particle concentration became $1\times10^8$ U/mL, to obtain a GFP recombinant virus diluted liquid.

The sphere-containing liquid obtained in the above (2) "Sphere culture" was mixed with 9 mL of PBS, to obtain liquid mixture. Next, the resulting liquid mixture was centrifuged at 350×g and 4° C. for 5 minutes, to remove the supernatant. Four to ten spheres after centrifugation were mixed with 90 μL of the viral infection medium obtained in Production Example 3. Ten microliters of the GFP recombinant virus diluted liquid was added to the resulting liquid mixture, to obtain a sphere-virus liquid mixture. The sphere-virus liquid mixture was incubated at 37° C. in 5% by volume carbon dioxide atmosphere, to infect each of sweat gland cells each constituting the sphere with a recombinant virus, thereby introducing GFP gene into a cell constituting the sphere. After 24 hours passed from the initiation of viral infection, a virus-infected sweat gland sphere was collected.

Reference Example 2

The dissociated sweat gland cells obtained in Reference Example 1 (1) "Production of sweat gland cell in dissociated state" were mixed with 9 mL of PBS. Next, the resulting liquid mixture was centrifuged at 350×g and 4° C. for 5 minutes, to remove the supernatant. Dissociated sweat gland cells of from $5\times10^2$ to $1\times10^5$ after centrifugation were mixed with 90 μL of the viral infection medium obtained in Production Example 3. Ten microliters of the GFP recombinant virus diluted liquid was added to the resulting liquid mixture, to obtain a sphere-virus liquid mixture. The sphere-virus liquid mixture was incubated at 37° C. in 5% by volume carbon dioxide atmosphere, to infect each of the dissociated sweat gland cells with the recombinant virus, thereby introducing GFP gene into each of the dissociated sweat gland cells. After 24 hours passed from the initiation of viral infection, the virus-infected sweat gland cells were collected.

Experimental Example 1

Fluorescence based on GFP in each of the virus-infected sweat gland spheres obtained in Reference Example 1 and the virus-infected sweat gland cells obtained in Reference Example 2 was observed under a fluorescence microscope. In addition, the virus-infected sweat gland spheres obtained in Reference Example 1 and the virus-infected sweat gland cells obtained in Reference Example 2 were observed under a confocal microscope.

Figure 1D:
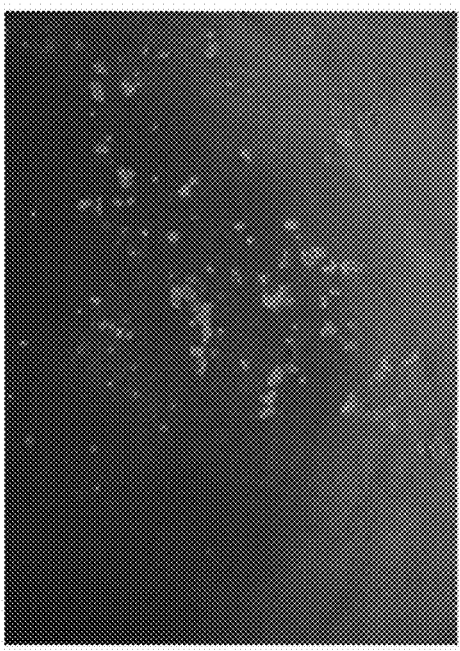
FIG. 1(D) is a photograph substituted for a drawing, showing results of confocal microscopy of the virus-infected sweat gland cells obtained in Reference Example 2.
Figure 1A:
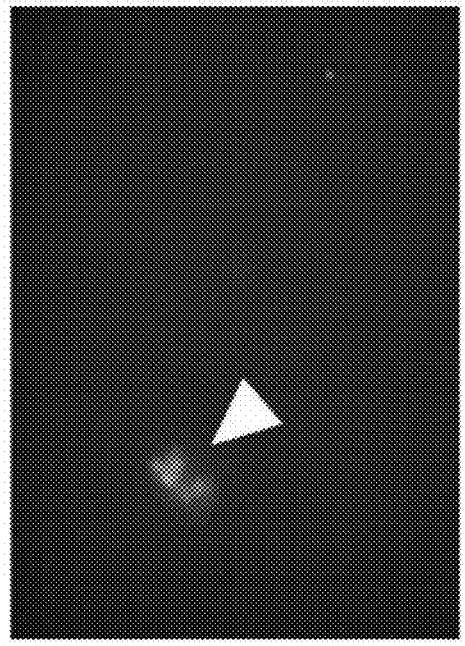
FIG. 1(A) is a photograph substituted for a drawing, showing results of fluorescence microscopy of the virus-infected sweat gland spheres obtained in Reference Example 1.
Figure 1C:
FIG. 1(C) is a photograph substituted for a drawing, showing results of phase-contrast microscopy of the virus-infected sweat gland spheres obtained in Reference Example 1.

Results of observation of fluorescence based on GFP in the virus-infected sweat gland spheres obtained in Reference Example 1 under a fluorescence microscope are shown in FIG. 1(A); results of observation of fluorescence based on GFP in the virus-infected sweat gland cells obtained in Reference Example 2 under a fluorescence microscope are shown in FIG. 1(B); results of observation of the virus-infected sweat gland spheres obtained in Reference Example 1 under a confocal microscope are shown in FIG. 1(C); and results of observation of the virus-infected sweat gland cells obtained in Reference Example 2 under a confocal microscope are Shown in FIG. 1(D). In the figures, the scale bar means 153 μm. In addition, the arrowhead in FIG. 1(A) shows the virus-infected sweat gland sphere, and the arrowhead in FIG. 1(B) shows the virus-infected sweat gland cell.

From the results shown in FIG. 1(A) and FIG. 1(C), it can be seen that GFP is expressed over the whole cells present on the surface of the virus-infected sweat gland sphere obtained in Reference Example 1. In contrast, it can be seen that there is almost no cell expressing GFP in the virus-infected sweat gland cells obtained in Reference Example 2. From these results, it can be seen that a gene can be introduced into a sweat gland cell with higher efficiency by infecting the sweat gland cell contained in the sphere with a virus, in a state of suspending the sphere in a medium, as compared with a case where a dissociated sweat gland cell is infected with a virus.

Example 1

The sphere-containing liquid obtained in Reference Example 1 (2) "Sphere culture" was mixed with 9 mL of PBS. Next, the resulting liquid mixture was centrifuged at 350×g and 4° C. for 5 minutes, to remove the supernatant. Four to ten spheres after centrifugation were mixed with 100 μL of the viral infection medium obtained in Production Example 3. To the resulting liquid mixture, 0.5 μL of an hTERT recombinant viral particle solution [manufactured by Applied Biological Materials Inc. under the trade name of High Titer Lentivirus containing hTERT, hTERT recombinant viral particle concentration: $1\times10^9$ U/mL] and 0.5 μL of an SV40Tt recombinant viral particle solution [manufactured by Applied Biological Materials Inc. under the trade name of High Titer Lentivirus expressing SV40 large and small T antigens, SV40Tt recombinant viral particle concentration: $1\times10^9$ U/mL] were added, thereby obtaining a sphere-virus liquid mixture. The sphere-virus liquid mixture was incubated at 37° C. in 5% by volume carbon dioxide atmosphere to infect sweat gland cells each constituting a sphere with the recombinant lentivirus, thereby introducing an immortalizing gene into each of the cells each constituting a sphere. After 24 hours passed from the initiation of viral infection, a virus-infected sweat gland spheres were collected.

Comparative Example 1

A sphere was obtained by carrying out in the same manner as in Reference Example 1 (1) "Production of sweat gland cells in dissociated state" and (2) "Sphere culture".

Experimental Example 2

(1) Sphere Subculture

It was defined as "single-time subculture" to carry out, the following processes (1-1) and (1-2).

(1-1) Production of Dissociated Sweat Gland Cells

The virus-infected sweat gland spheres obtained in Example 1 were mixed with 1 mL of the 0.5% by weight trypsin-EDTA solution obtained in Production Example 4 were mixed in a 15 mL-volume tube. The sweat gland cells each constituting the sweat gland were dissociated from each other by stirring the sweat gland in the tube for 3 minutes using a pipette, to obtain a dissociated sweat gland cell.

In addition, dissociated sweat gland cells were obtained in the same manner as in the above except that the sphere obtained in Comparative Example 1 was used in the above in place of the virus-infected sweat gland sphere obtained in Example 1.

(1-2) Sphere Culture

The dissociated sweat gland cells obtained in the above (1-1) "Production of dissociated sweat gland cells" were mixed with 9 mL of a 2% by weight FBS/PBS solution. The resulting liquid mixture was centrifuged at 350×g and 4° C. for 5 minutes, to remove the supernatant. One milliliter of the 5 U/mL dispase liquid obtained in Production Example 5 was added to the dissociated sweat gland cells in the tube. Thereafter, the dissociated sweat gland cells in the tube were stirred by using a pipette. Next, the liquid mixture containing dissociated sweat gland cells in the tube was allowed to pass through a cell strainer [mesh size: 40 μm, manufactured by Corning Incorporated under the trade name of Falcon (registered trademark) 40 μm Cell Strainer, Blue, Sterile, Individually Packaged], to obtain a suspension liquid of dissociated sweat gland cells.

Nine milliliters of a 2% by weight FBS/PBS solution was mixed with the suspension liquid of dissociated sweat gland cells in the tube. The resulting liquid mixture was centrifuged at 350×g and 4° C. for 5 minutes, to remove the supernatant. Next, the medium (II) obtained in Production Example 2 was added to the tube so that the dissociated sweat gland cell concentration became $2.3 \times 10^3$ cells to $2.7 \times 10^3$ cells/mL, to obtain a liquid mixture containing dissociated sweat gland cells. The resulting liquid mixture was put into a low-attachment plate [manufactured by Corning Incorporated under the trade name of Ultra-Low Attachment Plate, 24 well]. The dissociated sweat gland cells were incubated at 37° C. in 5% by volume carbon dioxide atmosphere in a suspended state in the medium (II) in the plate.

When spheres were formed after starting culture (incubation), the sphere was transferred to a 15 mL-volume tube. The sphere was centrifuged at 350×g and 4° C. for 5 minutes, to remove the liquid components. Next, 1 mL of a solution for cell recovery (manufactured by Corning Incorporated under the trade name of Cell Recovery Solution) was mixed with the sphere in the tube, to obtain a sphere-containing liquid. Thereafter, the tube containing the resulting sphere-containing liquid was left to stand on ice for 1 to 2 hours.

(1-3) Evaluation of Sphere-Forming Ability

A series of procedures consisting of the above (1-1) "Production of dissociated sweat gland cells" and the above (1-2) "Sphere culture" was repeated. Thereafter, sphere-forming ability was examined in presence or absence of sphere formation in the above (1-2) "Sphere culture".

Results of examining the relationship between sphere-forming ability and the passage number of the sweat gland cells contained in the virus-infected sweat gland sphere obtained in Example 1 are shown in FIG. 2(A), and results of examining the relationship between sphere-forming ability and passage number of the dissociated sweat gland cell obtained in Comparative Example 1 are shown in FIG. 2(B). In the figure, the arrowhead shows a sphere.

From the results shown in FIG. 2, it can be seen that the sweat gland cell contained in the virus-infected sweat gland sphere Obtained in Example 1 has sphere-forming ability even after 9 passages. In contrast, it can be seen that the dissociated sweat gland cells obtained in Comparative Example 1 does not have sphere-forming ability after 4 passages.

It was confirmed that the sweat gland cell contained in the virus-infected sweat gland sphere obtained in Example 1 formed a sphere even after 20 passages or more.

From the above results, it can be seen that an immortalized sweat gland cell can be obtained by infecting a sweat gland cell contained in a sphere in a state of suspending the sphere in a medium with a lentivirus carrying an immortalizing gene.

(2) Identification of Immortalized Sweat Gland Cell

Using anti-pan-cytokeratin antibody, a fluorescence-labeled secondary antibody against anti-pan-cytokeratin antibody, anti-α-SMA antibody and a fluorescence-labeled secondary antibody against α-SMA antibody, immunofluorescence staining of the dissociated sweat gland cell obtained in the above (1-1) "Production of dissociated sweat gland cells" and the dissociated sweat gland cell obtained in Comparative Example 1 was carried out. Next, intensity of fluorescence based on pan-cytokeratin in the dissociated sweat gland cell after immunofluorescence staining (hereinafter referred to as "fluorescence intensity A") and intensity of fluorescence based on α-SMA (hereinafter referred to as "fluorescence intensity B") were determined.

Next, the expression level of pan-cytokeratin in the cell to be evaluated was calculated by subtracting fluorescence intensity A in the dissociated sweat gland cell obtained in Comparative Example 1 from fluorescence intensity A in the cell to be evaluated. In addition, the expression level of α-SMA in the cell to be evaluated was calculated by subtracting fluorescence B in the dissociated sweat gland cell obtained in Comparative Example 1 from fluorescence intensity B in the cell to be evaluated.

Figure 3A:
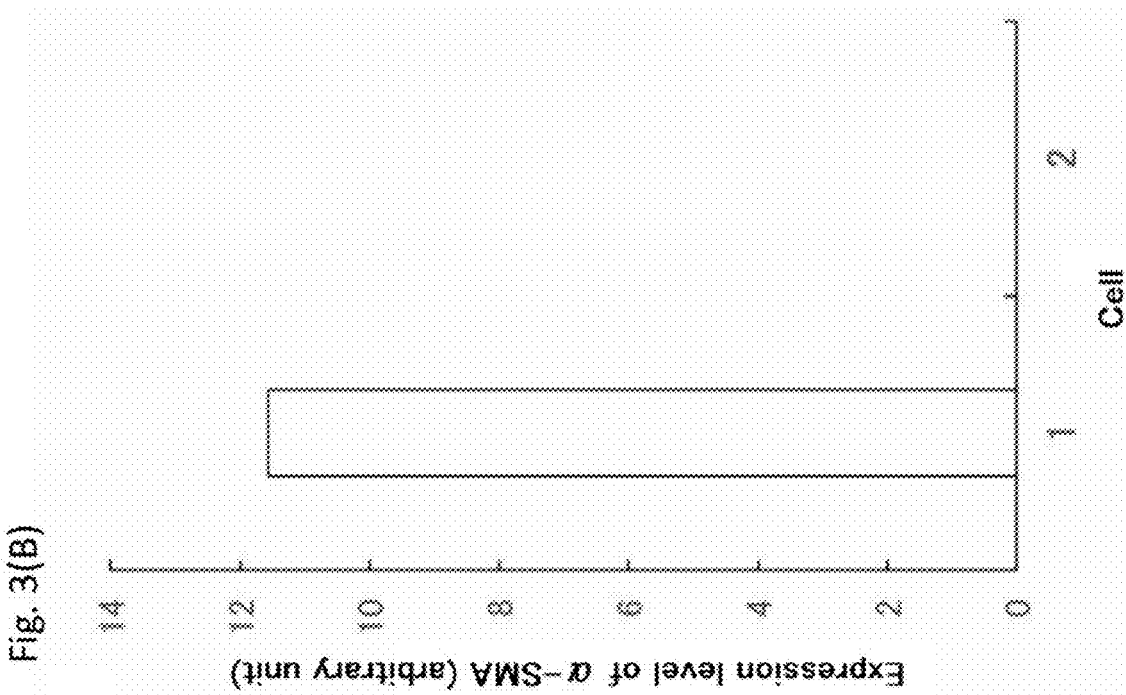
FIG. 3(A) is a graph showing results of examining the relationship between the kind of the cell and the expression level of pan-cytokeratin.
Figure 3B:
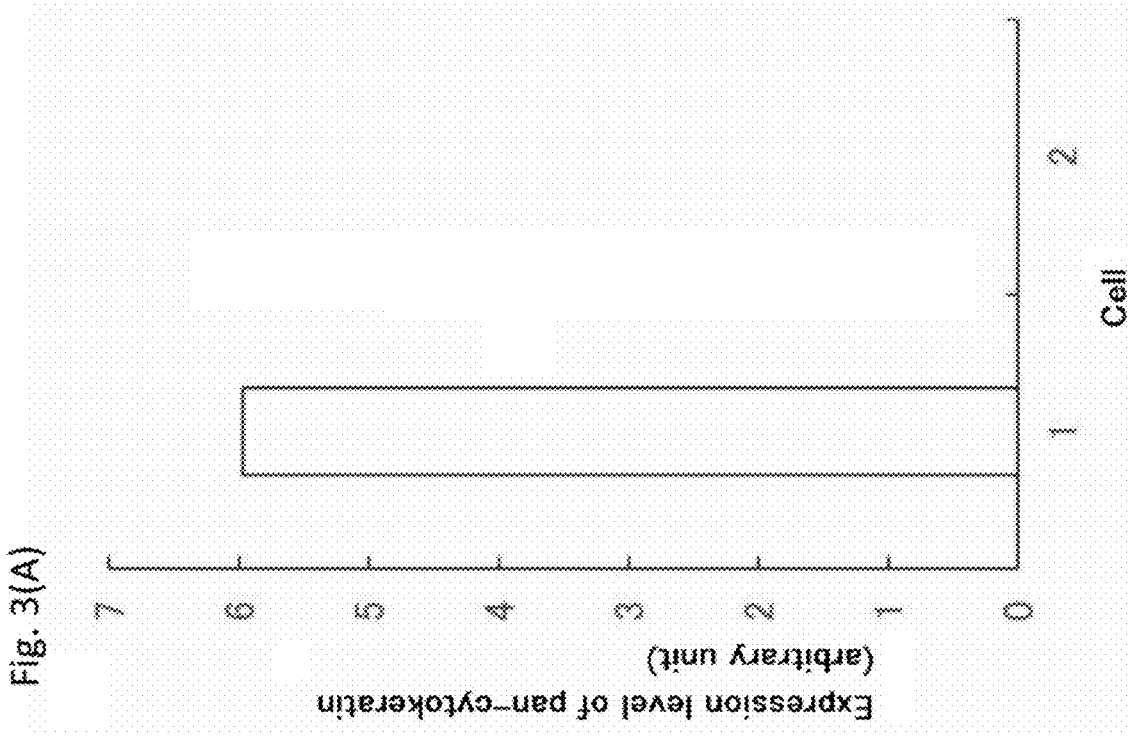
FIG. 3(B) is a graph showing results of examining the relationship between the kind of the cell and the expression level of α-SMA.

Results of examining the relationship between the kind of the cell and the expression level of pan-cytokeratin are shown in FIG. 3(A), and results of examining the relationship between the kind of the cell and the expression level of α-SMA are shown in FIG. 3(B). In FIG. 3(A), lane 1 shows the expression level of pan-cytokeratin in the immortalized sweat gland cell contained in the virus-infected sweat gland sphere obtained in Example 1, and lane 2 shows the expression level of pan-cytokeratin in the dissociated sweat gland cell obtained in Comparative Example 1. In FIG. 3(B), lane 1 shows the expression level of α-SMA in the immortalized sweat gland cell contained in the virus-infected sweat gland sphere obtained in Example 1, and lane 2 shows the expression level of α-SMA in the dissociated sweat gland cell obtained in Comparative Example 1.

From the results shown in FIG. 3(A) and FIG. 3(B), it can be seen that the immortalized sweat gland cell contained in the virus-infected sweat gland sphere obtained in Example 1 (see lane 1) expresses both pan-cytokeratin and α-SMA, which are myoepithelial cell markers. From these results, it can be seen that the immortalized sweat gland cell is an immortalized sweat gland myoepithelial cell. Accordingly, it can be seen that an immortalized sweat gland myoepithelial cell can be obtained by infecting a sweat gland cell contained in the sphere in a suspended state in a medium with a virus.

(3) Examination of Expression of Sweat Gland Cell Marker in Immortalized Sweat Gland Myoepithelial Cell Total RNA was extracted from the dissociated sweat gland cell obtained in the above (1-1) "Production of dissociated sweat gland cell". The resulting total RNA was added to DNase/RNase-free purified water [manufactured by Invitrogen under the trade name of UltraPure DNase/RNase-Free Distilled Water] so as to have a concentration of 1 µg/µL. Using a reverse transcription kit. [manufactured by QIAGEN under the trade name of QuatiTect Reverse Transcription Kit], cDNA was synthesized from the total RNA, to obtain a sample for determination.

Using the resulting sample for determination as a template, a PCR kit [manufactured by TOYOBO CO., LTD. under the trade name of THUNDERBIRD SYBR qPCR. Mix], a real-time PCR device [manufactured by Applied Biosystems under the trade name of ViiA7] and a primer pair for amplifying ATP1a1 gene, the number of cycles until the amount of synthesized nucleotides each of which template was cDNA of ATP1a1 gene reached the threshold (hereinafter referred to as "$Ct_A$ value") was determined. In addition, the number of cycles until the amount of a synthesized nucleotide obtained by using cDNA for the control gene as a template reached the threshold (hereinafter referred to as "$Ct_B$ value") was determined in the same manner as in the above except that a primer pair for amplifying GAPDH gene which is a control gene, was used in the above in place of the primer pair for amplifying ATP1a1 gene. Thermal profile in the real-time RT-PCR method is a treatment at 95° C. for 1 minute and subsequent 40-cycle reaction, in which 1 cycle is a denaturation at 95° C. for 5 seconds; annealing at 55° C. for 10 seconds; and extension at 72° C. for 20 seconds.

Using the $Ct_A$ value and $Ct_B$ value, in accordance with the equation (I):
[Formula 1]
$$[\text{Expression value}]=(\tfrac{1}{2})^{CtA-CtB} \qquad (I)$$

the expression value of ATP1a1 gene in the immortalized sweat gland myoepithelial cell contained in the virus-infected sweat gland sphere obtained in Example 1 was calculated.

In addition, the expression value of ATP1a1 gene in the control cell was calculated in the same manner as in the above except that a skin epidermal cell not expressing ATP1a1 gene was used as a control cell in the above in place of the dissociated sweat gland cell obtained in (1-1) "Production of dissociated sweat gland cell".

A corrected expression value of ATP1a1 gene in the immortalized sweat gland myoepithelial cell was calculated by subtracting the expression value of ATP1a1 gene in the control cell from the expression value of ATP1a1 gene in the immortalized sweat gland myoepithelial cell. Next, it was evaluated whether or not the immortalized sweat gland myoepithelial cell expressed ATP1a1 gene, in accordance with the following evaluation criteria, on the basis of the corrected expression value.

Evaluation Criteria

"The immortalized sweat gland myoepithelial cell expresses ATP1a1 gene" . . . the corrected expression value is a "positive value".

"The immortalized sweat gland myoepithelial cell does not express ATP1a1 gene" . . . the corrected expression value is "0" or a "negative value".

As a result, the expression value of ATP1a1 gene in the immortalized sweat gland myoepithelial cell contained in the virus-infected sweat gland sphere obtained in Example 1 was a positive value. Thus, it was found that the immortalized sweat gland myoepithelial cell expressed ATP1a1 gene. ATP1a1 one of sweat gland myoepithelial cell markers. Accordingly, it can be seen that the immortalized sweat gland myoepithelial cell contained in the virus-infected sweat gland sphere obtained in Example 1 expressed a sweat gland myoepithelial cell marker.

Example 2

(1) Production of Sweat Gland-Containing Tissue

Used was as a skin tissue, a skin tissue of an eyelid excised within 48 hours, which had been refrigerated in cold storage immediately after excision from a living body (a 41-year-old human). The skin tissue was immersed in 10 !AM Neutral Red-containing PBS, thereby incorporating Neutral Red into a sweat gland in the skin tissue. Next, tissue pieces each containing a sweat gland was separated from the skin tissue using tweezers and scissors under an optical microscope. The separated tissue pieces were gathered in aseptic PBS in a 15 mL-volume tube. The tissue pieces were washed by lightly shaking PBS containing the tissue pieces and thereafter centrifuging the PBS at. 350 x g and 4° C. for 5 minutes, to remove the supernatant.

Ten milliliters of the medium (I) obtained in Production Example 1 was mixed with the tissue pieces in the tube. Next, collagenase II was added to the medium (I) in the tube so as to have a concentration of 600 U/mL. Thereafter, the tissue piece in the tube was incubated at. 37° C. in 5% by volume carbon dioxide atmosphere while rotating the tube by a rotator, to remove collagenous fibers from the tissue piece.

After 4 hours passed from the initiation of incubation, the medium (I) and the tissue piece from which collagenous fibers had been removed in the tube were transferred to a 10 cm-diameter dish. The tissue pieces on the dish were collected by using a pipette under an optical microscope. The collected tissue pieces were gathered in aseptic PBS in a 15 mL-volume tube. The tissue pieces were washed by lightly shaking PBS containing the tissue piece and thereafter centrifuging the PBS at 350×g and 4° C. for 5 minutes, to remove the supernatant.

The tissue pieces after washing were mixed with 10 mL of medium (I) in a 15 mL-volume tube. Dispase was added to the liquid mixture so as to have a concentration of 1 U/mL. After transferring the resulting liquid mixture to a 10 cm-diameter dish, the liquid mixture was incubated in a stationary state at 37° C. in 5% by volume carbon dioxide atmosphere. After 8 hours passed from the initiation of incubation, 10 mL of a 2% by weight FBS/PBS solution was added to the liquid mixture to dilute the liquid mixture, to stop the enzymatic reaction.

The tissue pieces on the dish were collected by using a pipette under an optical microscope. The collected tissue pieces were gathered in aseptic PBS in a 15 mL-volume tube. The tissue pieces were washed by lightly shaking PBS containing the tissue pieces and thereafter centrifuging the PBS at 350×g and 4° C. for 5 minutes, to obtain a sweat gland-containing tissue.

(2) Viral Infection

The hTERT recombinant viral particle solution and the SV40Tt recombinant viral particle solution were diluted with the viral infection medium so that the hTERT recombinant viral particle concentration became $1\times10^8$ U/mL and the SV40Tt recombinant viral particle concentration became $1\times10^8$ U/mL, to obtain a diluted liquid of immortalizing gene-containing recombinant viruses.

The sweat gland-containing tissue obtained in (1) "Production of sweat gland-containing tissue" was mixed with 9 mL of PBS. Next, the resulting liquid mixture was centrifuged at 350×g and 4° C. for 5 minutes, to remove the supernatant. The sweat gland-containing tissue containing 4 to 10 sweat glands after centrifugation was mixed with 100 µL of the viral infection medium obtained in Production Example 3. Two microliters of the diluted liquid of immortalizing gene-containing recombinant viruses was added to the resulting liquid mixture, to obtain a tissue-virus liquid mixture. The tissue-virus liquid mixture was incubated at 37° C. in 5% by volume carbon dioxide atmosphere, to infect sweat gland cells each constituting the sweat gland with a recombinant lentivirus. Furthermore, to the resulting mixture, 2 µL of the diluted liquid of immortalizing gene-containing recombinant viruses contained in the sweat gland-containing tissue was added every 30 minutes to 12 hours from the start of viral infection, thereby infecting the sweat gland cell contained in the sweat gland-containing tissue with a recombinant virus, to introduce an immortalizing gene into a sweat gland cell. After 33 hours passed from the initiation of viral infection, a virus-infected tissue was collected.

Experimental Example 3

Sphere subculture was carried out in the same manner as in Experimental Example 2 (1) "Sphere subculture" except that in Experimental Example 2 (1) "Sphere subculture", the virus-infected tissue obtained in Example 2 was used in place of the virus-infected sweat gland sphere obtained in Example 1.

Results of examining the relationship between sphere-forming ability and passage number of the sweat gland cell contained in the virus-infected tissue obtained in Example 2 are shown in FIG. 4(A), and results of examining the relationship between sphere-forming ability and passage number of the dissociated sweat gland cell obtained in Comparative Example 1 are shown in FIG. 4(B). In the figure, the arrowhead shows a sphere.

From the results shown in FIG. 4, it can be seen that the sweat gland cell contained in the virus-infected tissue obtained in Example 2 could form a sphere even after the 7th passages. To the contrary, the dissociated sweat gland cell obtained in Comparative Example 1 could not form a sphere after the 4th subculture.

Incidentally, it was confirmed that the sweat gland cell contained in the virus-infected tissue obtained in Example 2 formed a sphere even after 12 passages or more. In addition, when presence or absence of expression of pan-cytokeratin and α-SMA in the sweat gland cell contained in the virus-infected tissue obtained in Example 2 was examined, it was confirmed that pan-cytokeratin and α-SMA were expressed.

From the above results, it can be seen that an immortalized sweat gland myoepithelial cell can be obtained by infecting a sweat gland myoepithelial cell contained in a sweat gland-containing tissue with a virus in a state of suspending the sweat gland-containing tissue in a medium.

Reference Examples 3 to 7

(1) Production of Dissociated Sweat Gland Cells

Dissociated sweat gland cells were obtained in the same manner as in Reference Example 1 (1) "Production of sweat gland cells in dissociated state" except that in Reference Example 1 (1) "Production of sweat gland cells in dissociated state", a skin tissue of an eyelid of a 20-year-old human (Reference Example 3), a skin tissue of an eyelid of a 71-year-old human (Reference Example 4), a skin tissue of an eyelid of a 74-year-old human (Reference Example 5), a skin tissue of an abdomen of a 51-year-old human (Reference Example 6) or a skin tissue of an abdomen of a 55-year-old human (Reference Example 7) was used in place of a skin tissue of an eyelid of a 68-year-old human.

(2) Sphere Culture

A sphere-containing liquid was obtained in the same manner as in Reference Example 1 (2) "Sphere culture" of except that in Reference Example 1 (2), dissociated sweat gland cell obtained in (1) "Production of dissociated sweat gland cell" of Reference Examples 3 to 7 were used in place of the dissociated sweat gland cell obtained in Reference Example 1 (1) "Production of dissociated sweat gland cells".

Examples 3 to 7

Virus-infected sweat gland spheres were obtained in the same manner as in Example 1 except that the sphere-containing liquid obtained in Reference Example 3 (Example 3), the sphere-containing liquid obtained in Reference Example 4 (Example 4), the sphere-containing liquid obtained in Reference Example 5 (Example 5), the sphere-containing liquid obtained in Reference Example 6 (Example 6) or the sphere-containing liquid obtained in Reference Example 7 (Example 7) was used in Example 1 in place of the sphere-containing liquid obtained in Reference Example 1 (2) "Sphere culture".

Comparative Examples 3 to 7

Dissociated sweat gland cells were obtained in the same manner as in Reference Example 1 (1) "Production of sweat gland cells in dissociated state" except that in Reference Example 1 (1) "Production of sweat gland cells in dissociated state", a skin tissue of an eyelid of a 20-year-old human (Comparative Example 3), a skin tissue of an eyelid of a 71-year-old human (Comparative Example 4), a skin tissue of an eyelid of a 74-year-old human (Comparative Example 5), a skin tissue of an abdomen of a 51-year-old human (Comparative Example 6) or a skin tissue of an abdomen of a 55-year-old human (Comparative Example 7) was used in place of a skin tissue of an eyelid of a 68-year-old human.

Experimental Example 4

The sphere subculture was carried out in the same manner as in

Experimental Example 2 (1) "Sphere subculture" except that in Experimental Example 2 (1) "Sphere subculture", each of the virus-infected tissues obtained in Examples 3 to 7 were used in place of the virus infected sweat gland sphere obtained in Example 1.

In addition, the sphere subculture was carried out in the same manner as in Experimental Example 2 (1) "Sphere subculture" except that in Experimental Example 2 (1) "Sphere subculture", each of the dissociated sweat gland cells obtained in Comparative Examples 3 to 7 was used in place of the dissociated sweat gland cells obtained in Comparative Example 1. Passage number of a cell having sphere-forming ability is shown in Table 1.

TABLE 1

| Example or Comparative Example | Source of skin tissue | Passage number of cell having sphere-forming ability (passage) |
|---|---|---|
| Example 3 | Eyelid of 20-year-old human | 19 |
| Example 4 | Eyelid of 71-year-old human | 18 |
| Example 5 | Eyelid of 74-year-old human | 40 |
| Example 6 | Abdomen of 51-year-old human | 26 |
| Example 7 | Abdomen of 55-year-old human | 19 |
| Comparative Example 3 | Eyelid of 20-year-old human | 2 |
| Comparative Example 4 | Eyelid of 71-year-old human | 3 |
| Comparative Example 5 | Eyelid of 74-year-old human | 2 |
| Comparative Example 6 | Abdomen of 51-year-old human | 2 |
| Comparative Example 7 | Abdomen of 55-year-old human | 2 |

From the results shown in Table 1, it can be seen that the sweat gland cells contained in the virus-infected sweat gland spheres obtained in Examples 3 to 7 have sphere-forming ability even after at least 18 passages. In contrast, it can be seen that the dissociated sweat gland cells obtained in Comparative Examples 3 and 5 to 7 lose sphere-forming ability after 2 passages. In addition, it can be seen that the dissociated sweat gland cell obtained in Comparative Example 4 loses sphere-forming ability after 3 passages.

From these results, it can be seen that an immortalized sweat gland cell can be obtained by infecting a sweat gland cell contained in a sphere with a virus, in a state of suspending the sphere in a medium, regardless of the kind of the source of the skin tissue.

Each of the spheres used in Examples 1 and 3 to 7 and the sweat gland-containing tissue used in Example 2 has a structure in which a sweat gland myoepithelial cell included in the structure is exposed on the surface of the structure. Accordingly, it can be seen that an immortalizing gene can be introduced into a sweat gland myoepithelial cell by infecting the cell structure with a virus carrying an immortalizing gene while culturing in a suspended state in a medium, the cell structure in which the sweat gland myoepithelial cell included in the cell structure is exposed on the surface of the cell structure.

Experimental Example 5

(1) Sphere Subculture

It was defined as "single-time subculture" to carry out the following processes (1-1) and (1-2):

(1-1) Production of Dissociated Sweat Gland Cells

Dissociated sweat gland cells were obtained in the same manner as in Experimental Example 2 (1-1) "Production of dissociated sweat gland cells" except that in Experimental Example 2 (1-1) "Production of dissociated sweat gland cells", the virus-infected sweat gland spheres obtained in Examples 3 to 7 were used in place of the virus-infected sweat gland spheres obtained in Example 1.

(1-2) Sphere Culture

A part of the dissociated sweat gland cells obtained in (1-1) "Production of sweat gland cell" (cell number A of dissociated sweat gland cells) was mixed with 9 mL of a 2% by weight FBS/PBS solution. The resulting liquid mixture was centrifuged at 350×g and 4° C. for 5 minutes, to remove the supernatant. After adding 1 mL of the 5 U/mL dispase liquid to the dissociated sweat gland cells obtained in Production Example 5 in the tube, the dissociated sweat gland cells in the tube were stirred by using a pipette. Next, the aggregated cells were removed by allowing the liquid mixture containing dissociated sweat gland cells in the tube was to pass through a cell strainer [mesh size: 40 µm, manufactured by Corning Incorporated under the trade name of Falcon (registered trademark) 40 µm Cell Strainer, Blue, Sterile, Individually Packaged], to obtain a suspension liquid of dissociated sweat gland cells.

Nine milliliters of a 2% by weight FBS/PBS solution was mixed with the suspension liquid of dissociated sweat gland cells in the tube. The resulting liquid mixture was centrifuged at 350×g and 4° C. for 5 minutes to remove the supernatant.

Next, the resulting dissociated sweat gland cells were added to the medium (II) Obtained in Production Example 2 so as to have a concentration of $2.5 \times 10^3$ cells/mL, to obtain a liquid mixture containing dissociated sweat gland cells. The resulting liquid mixture was put into a low attachment plate [manufactured by Corning Incorporated under the trade name of Ultra-Low Attachment Plate, 24 well]. The dissociated sweat gland cells were incubated at 37° C. in 5% by volume carbon dioxide in a suspended state in the medium (II) in the plate.

When spheres were formed after starting culture (incubation), the sphere was transferred to a 15 mL-volume tube.

The sphere was centrifuged at 350×g and 4° C. for 5 minutes, to remove liquid components. Next, 1 mL of a solution for cell recovery (manufactured by Corning Incorporated under the trade name of Cell Recovery Solution) was mixed with the sphere in the tube, to obtain a sphere-containing liquid. Thereafter, the tube containing the resulting sphere-containing liquid was left to stand on ice for 1 to 2 hours.

(1-3) Evaluation of Cell Proliferative Capacity

A series of operations consisting of the (1-1) "Production of dissociated sweat gland cell" and (1-2) "Sphere culture" was repeated until sphere formation stopped.

Using the cell number A and the number of dissociated sweat gland cell obtained in the above (1-1) "Production of dissociated sweat gland cell" at the time of sphere subculture of which passage number was n (n shows a positive integer) (hereinafter referred to as "cell number B"), the multiplying factor of cell proliferation ($K_X$) between each subculture was calculated in accordance with the formula (II):

[multiplying factor of cell proliferation between each subculture ($K_X$)]=[cell number B]/[cell number A]   (II).

Using the multiplying factor of cell proliferation ($K_X$) between each subculture, the total multiplying factor of cell proliferation of each of the sweat gland cells contained in the spheres obtained in Examples 3 to 7 in accordance with the formula (III):

[total multiplying factor of cell proliferation]=$K_1$× $K_2$ . . . ×$K_X$   (III)

wherein X shows a positive integer. The results are shown in Table 2.

TABLE 2

| Example or Comparative Example | Total multiplying factor of cell proliferation (times) |
|---|---|
| Example 3 | $6.8 \times 10^{13}$ |
| Example 4 | $2.6 \times 10^{13}$ |
| Example 5 | $5.8 \times 10^{28}$ |
| Example 6 | $3.4 \times 10^{25}$ |
| Example 7 | $1.4 \times 10^{18}$ |
| Comparative Example 3 | $4.1 \times 10^{-1}$ |
| Comparative Example 4 | $2.9 \times 10^{-1}$ |
| Comparative Example 5 | — |
| Comparative Example 6 | 2.1 |
| Comparative Example 7 | $6.7 \times 10^{-1}$ |

The mark of "—" shows that the factor was uncalculatable.

From the results shown in Table 2, it can be seen that the total multiplying factor of cell proliferation of each of the immortalized sweat gland cells contained in the spheres obtained in Examples 3 to 7 was $2.6 \times 10^{13}$ times or more. In contrast, the total multiplying factor of cell proliferation of the sweat gland cell which had not been immortalized was 2.1 times or less. From these results, it can be seen that the cell proliferative capacity of each of the immortalized sweat gland cells contained in the spheres obtained in Examples 3 to 7 was improved as compared with the cell proliferative capacity of the sweat gland cell which had not been immortalized.

Experimental Example 6

(1) Production of Dissociated Sweat Gland Cells

A dissociated sweat gland cell was obtained in the same manner as in Experimental Example 2 (1-1) "Production of dissociated sweat gland cells" except that in Experimental Example 2 (1-1) "Production of dissociated sweat gland cells", the sphere obtained in Example 3 (Experiment number 1), the sphere obtained in Example 4 (Experiment number 2) or the sphere obtained in Example 5 (Experiment number 3) was used in place of the virus-infected sweat gland sphere obtained in Example 1. Additionally, in the above, a sphere of which passage number was 5 was used as the sphere obtained in Example 3; a sphere of which passage number was 8 was used as the sphere obtained in Example 4; and a sphere of which passage number was 14 was used as the sphere obtained in Example 5.

(2) Cryopreservation of Dissociated Sweat Gland Cell

The dissociated sweat gland cells obtained in Experimental Example 6 (1) "Production of dissociated sweat gland cells" were suspended in 1 mL of cryopreservation liquid [manufactured by Takara Bio Inc. under the trade name of CELLBANKER (registered trademark) 1plus] so that the dissociated sweat gland cell concentration was as shown in Table 3. The resulting suspension was frozen in a freezer kept at −80° C. to freeze the suspension, to obtain a frozen cell. The resulting frozen cell was stored in a freezer kept at −80° C. or in liquid nitrogen for a given preservation period shown in Table 3. Thereafter, the frozen product was thawed, to obtain thawed cells of Experiment numbers 1 to 3. The number of the resulting thawed cells was determined. Hereinafter, the number of thawed cells was used as the cell number C.

TABLE 3

| Experiment No. | Concentration (cell/mL) | Preservation period (day) |
|---|---|---|
| 1 | $4.0 \times 10^5$ | 75 |
| 2 | $5.3 \times 10^4$ | 129 |
| 3 | $4.5 \times 10^4$ | 50 |

(2) Sphere Formation

A sphere-containing liquid A of Experiment numbers 1 to 3 was obtained in the same manner as in Experimental Example 2 (1-2) "Sphere formation" except that in Experimental Example 2 (1-2) "Sphere culture", the thawed cells obtained in Experimental Example 6 (2) "Cryopreservation of dissociated sweat gland cell" were used in place of the dissociated sweat gland cells obtained in Experimental Example 2 (1-1) "Production of dissociated sweat gland cells".

(3) Sphere Subculture

It was defined as "single-time subculture" to carry out the following (3-1) and (3-2).

(3-1) Production of Dissociated Sweat Gland Cell

Dissociated sweat gland cells of Experimental Example 3 were obtained in the same manner as in Experimental Example 2 (1-1) "Production of dissociated, sweat gland cell" except that the sphere-containing liquid A of Experiment number 3 in the sphere-containing liquids A obtained in Experimental Example 6 (2) "Sphere formation" was used in place of the virus-infected sweat gland, sphere obtained in Example 1 in Experimental Example 2 (1-1) "Production of dissociated sweat gland cell".

(3-2) Sphere Culture

A sphere-containing liquid B of Experiment number 3 was obtained in the same manner as in Experimental Example 2 (1-2) "Sphere culture" except that the dissociated sweat gland cells obtained in Experimental Example 6 (3-1) "Production of dissociated sweat gland cells" was used in place of the dissociated sweat gland cells obtained in Experimental Example 2 (1-1) "Production of dissociated sweat gland cells" in Experimental Example 2 (1-2) "Sphere culture".

(3-3) Evaluation of Cell Proliferative Capacity

Subcultured cells were obtained in the same manner as in Experimental Example 2 (1-1) "Production of dissociated sweat gland cell" except that the sphere contained in the sphere-containing liquid A of Experiment number 1, the sphere contained in the sphere-containing liquid A of Experiment number 2 and the sphere contained in the sphere-containing liquid B of Experiment number 3 were used in place of the virus-infected sweat gland sphere obtained in Example 1 in Experimental Example 2 (1-1) "Production of dissociated sweat gland cell". The number of the resulting subcultured cells (hereinafter referred to as "the cell number D") was determined.

Next, using the cell number C and the cell number D, the multiplying factor of cell proliferation in a case where each of the immortalized sweat gland cells contained in the spheres of Experiment numbers 1 to 3 was cryopreserved was calculated in accordance with the equation (IV):

$$[\text{Multiplying factor of cell proliferation}]=[\text{cell number D}]/[\text{cell number C}] \quad (IV).$$

The evaluation results of the multiplying factor of cell proliferation are shown in Table 4. In the table, the evaluation criteria of cell proliferative capacity and sphere-forming ability are as follows:

Evaluation Criteria of Cell Proliferative Capacity

+: The multiplying factor of cell proliferation calculated in accordance with the formula (IV) is 1 or more.

−: The multiplying factor of cell proliferation calculated in accordance with the formula (IV) is 1 or less.

Evaluation Criteria of Sphere-Forming Ability

+: Sphere formation is confirmed under an optical microscope.

−: Sphere formation is not confirmed under an optical microscope.

TABLE 4

| Ex. No. | Passage number (passage) | Number of thawed cells (cell) | Number of subcultured cells (cell) | Multiplying factor of cell proliferation (times)/culture period (day) | Cell proliferative capacity | Sphere-forming ability |
| --- | --- | --- | --- | --- | --- | --- |
| 1 | 6 | $1.2 \times 10^5$ | $5.5 \times 10^5$ | 4.6/8 | + | + |
| 2 | 9 | $2.0 \times 10^4$ | $6.4 \times 10^5$ | 32/12 | + | + |
| 3 | 15 | $7.5 \times 10^3$ | $3.5 \times 10^4$ | 4.7/14 | + | + |

From the results shown in Table 4, it can be seen that the immortalized sweat gland cells contained in the spheres of Experiment numbers 1 to 3 have favorable cell proliferative capacity and favorable sphere-forming ability. From these results, each of the immortalized sweat gland cells contained in the spheres of Experiment numbers 1 to 3 are excellent in cell proliferative capacity and sphere-forming ability even after cryopreserved. Thus, it can be seen that the immortalized sweat gland cells contained in the spheres of Experiment numbers 1 to 3 are excellent in preservation stability.

As explained above, it can be seen that an immortalized sweat gland myoepithelial cell can be obtained by introducing an immortalizing gene into a sweat gland myoepithelial cell while culturing in a suspended state in a medium, a cell structure in which the sweat gland myoepithelial cell included in the cell structure is exposed on the surface of the cell structure. In addition, it can be seen that the immortalized sweat gland myoepithelial cell obtained by carrying out the above-mentioned operations has the same function as that of the sweat gland myoepithelial cell and the same property as a sweat gland myoepithelial cell in a living body, and that the cell having the above function and the above property can be propagated for a long period of time. Accordingly, it is expected that the immortalized sweat gland myoepithelial cell of the present invention and the method for producing the immortalized sweat gland myoepithelial cell of the present invention is used for development of an external preparation such as an antiperspirant and a deodorant agent and an agent for improving the function of a sweat gland and the like.

The invention claimed is:

1. A method of producing an immortalized sweat gland myoepithelial cell, comprising the steps of:
   culturing a population of sweat gland cells in a suspended state in a medium, to form a sphere in which sweat gland myoepithelial cells are exposed on a surface of the sphere;
   introducing an immortalizing gene into the sweat gland myoepithelial cells present in the sphere while culturing the sphere in a suspended state in a medium to obtain a transgenic sphere; and
   culturing the transgenic sphere in a suspended state in a medium to obtain an immortalized sweat gland myoepithelial cell, wherein the immortalizing gene is an hTERT gene, a SV40T (large T) antigen gene, and a SV40t (small t) antigen gene.

2. The method of claim 1, wherein the immortalizing gene is comprised in a viral vector.

* * * * *